US007659836B2

(12) United States Patent
Novak

(10) Patent No.: US 7,659,836 B2
(45) Date of Patent: Feb. 9, 2010

(54) DEVICE FOR COMMUNICATING WITH A VOICE-DISABLED PERSON

(75) Inventor: Kathleen Novak, Wilmington, DE (US)

(73) Assignee: AstraZeneca AB, Sodertalje (SE)

( * ) Notice: Subject to any disclaimer, the term of this patent is extended or adjusted under 35 U.S.C. 154(b) by 924 days.

(21) Appl. No.: 11/186,159

(22) Filed: Jul. 20, 2005

(65) Prior Publication Data

US 2007/0021153 A1    Jan. 25, 2007

(51) Int. Cl.
*H03M 11/00*    (2006.01)
(52) U.S. Cl. .................. 341/20; 341/22; 340/825.19; 434/112
(58) Field of Classification Search ............ 341/20, 341/22; 345/173, 174; 340/825.19, 407.2; 434/111–116, 308–312
See application file for complete search history.

(56) References Cited

U.S. PATENT DOCUMENTS

| 3,651,512 | A |   | 3/1972  | Summers |
| 3,831,296 | A | * | 8/1974  | Hagle ........................ 434/112 |
| 3,925,779 | A | * | 12/1975 | Gerstenhaber .............. 345/1.1 |
| 5,392,735 | A | * | 2/1995  | Xitco et al. ................. 119/712 |
| 5,856,819 | A | * | 1/1999  | Vossler ....................... 345/102 |
| 5,949,643 | A | * | 9/1999  | Batio ..................... 361/679.27 |
| 5,984,368 | A |   | 11/1999 | Cain |
| 6,056,549 | A | * | 5/2000  | Fletcher ..................... 434/112 |
| 6,339,410 | B1 |  | 1/2002  | Milner et al. |
| 6,422,875 | B1 |  | 7/2002  | Patak et al. |
| 6,861,946 | B2 | * | 3/2005 | Verplaetse et al. ....... 340/407.2 |
| D561,901 | S |   | 2/2008  | Novak et al. |
| 2005/0062726 | A1 | * | 3/2005 | Marsden et al. ............ 345/173 |
| 2005/0237702 | A1 | * | 10/2005 | Kee et al. .................... 361/681 |

FOREIGN PATENT DOCUMENTS

| DE | 29704391 | 7/1998 |
| GB | 1473043  | 5/1977 |

OTHER PUBLICATIONS

Patak et al., "Patient's Reports of Health Care Practitioner Interventions Related to Communication During Mechanical Ventilation," *Heart & Lung—The Journal of Acute and Critical Care* (2004) 33(5):308-320.
Office Action dated Apr. 1, 2009 received in counterpart U.S. Appl. No. 11/996,085. 4 pgs.

* cited by examiner

*Primary Examiner*—Timothy Edwards, Jr.
(74) *Attorney, Agent, or Firm*—Pepper Hamilton LLP

(57) ABSTRACT

The present invention provides a device for communicating with a voice-disabled person. The device includes, generally, a housing, a plurality of means for receiving physical input, each physical input receiving means generating a specified response signal upon being physically manipulated, a display means, and means for receiving the response signals and converting the response signals into a corresponding visual representation on the display means.

15 Claims, 4 Drawing Sheets

_US 7,659,836 B2_

DEVICE FOR COMMUNICATING WITH A VOICE-DISABLED PERSON

FIELD OF THE INVENTION

The present invention is directed, in part, to devices for communicating with voice-disabled persons or with persons having difficulty speaking due to a particular disease or condition.

BACKGROUND OF THE INVENTION

A person may become voice-disabled or have difficulty speaking due to, for example, a disease condition or because of a surgical procedure requiring, for example, intubation. Such voice-disabled persons may be present in a hospital, clinic, hospice, or even in the person's home. Communication for such a person can resort to reading of lips, nodding of heads, and squeezing of hands to communicate with family and health care professionals. Without effective communication, the voice-disabled person may not receive the standard of care he or she would otherwise receive had he or she been able to communicate effectively. The lack of effective communication may also create unnecessary levels of anxiety for the voice-disabled person. Health care professionals ask the voice-disabled person many questions relating to their prognosis and progress which may not be adequately answered. In addition, other problems arise due to the ineffective communication from the voice-disabled person. For example, localized areas of pain are often misdiagnosed, resulting in over-medication or medication of an area which is not the source of pain. Proper and essential treatment given in an adequate and timely manner will help resolve or prevent many post-operative complications and decrease the voice-disabled person's length of stay in a health care environment. Providing the voice-disabled person with a clear and precise means of communication is, thus, greatly desired. Accordingly, there has been a need for a communication device for a voice-disabled person. In addition, a communication device is needed which accomplishes the desired function while being easy to manufacture and use while remaining cost effective. The present invention fulfills these needs and provides other related advantages.

SUMMARY OF THE INVENTION

The present invention provides a device which facilitates communication between a voice-disabled person and another person. In some embodiments, the communication device is hand-held.

In some embodiments, the hand-held communication device comprises a housing comprising a first and second side; a plurality of means for receiving physical input, each physical input receiving means generating a specified response signal upon being physically manipulated; a display means comprising a first and second side; and means for receiving the response signals and converting the response signals into a corresponding visual representation on the display means.

In some embodiments, the means for receiving physical input comprises a key pad comprising one or more keys. The key pad can be located on the first side of the housing, on the second side of the housing, or on both the first and second side of the housing. The keys of the key pad can comprise a descriptive word, phrase, or picture printed onto at least one surface thereof. For example, the key pad can comprise a key for each letter of the alphabet, a key for numerals 0 to 9, or a descriptive word, phrase, or picture selected from the group consisting of: doctor, nurse, hot, cold, "what day is it?", up, down, hungry, thirsty, family, turn, bed, chair, toilet, sit, bath, "what time is it?", sleep, sick, TV, dizzy, book, pillow, yes, no, on, off, "where am I?", glasses, lotion, hairbrush, light, cannot breath, paper and pencil, or any combination thereof.

In some embodiments, the display means is a display screen, which can be pivotally mounted to the housing. The display screen can be an LCD screen. The display screen can display visual representations on the first and second side of the display screen.

In some embodiments, the means for receiving the response signals and converting the response signals into a corresponding visual representation on the display means comprises electronic circuitry. The electronic circuitry can be computer controlled.

In some embodiments, the hand-held communication device further comprises a pain indicator, a battery compartment, an AC adapter, a battery level indicator, or any combination thereof.

In some embodiments, the hand-held communication device further comprises a recharging station.

Other features and advantages of the present invention will become apparent from the following more detailed description, taken in conjunction with the accompanying drawings which illustrate, by way of example, the principles of the invention.

DESCRIPTION OF EMBODIMENTS

The present invention provides a hand-held communication device 10 that can be used for communicating with a voice-disabled person or a person who has difficulty speaking due to, for example, a disease or condition. A person may become voice-disabled or have difficulty speaking due to, for example, a disease condition or because of a surgical procedure requiring, for example, intubation. The voice-disabled person or person having difficulty speaking may be in a hospital, clinic, hospice, at home, or any other location.

Figure 1:
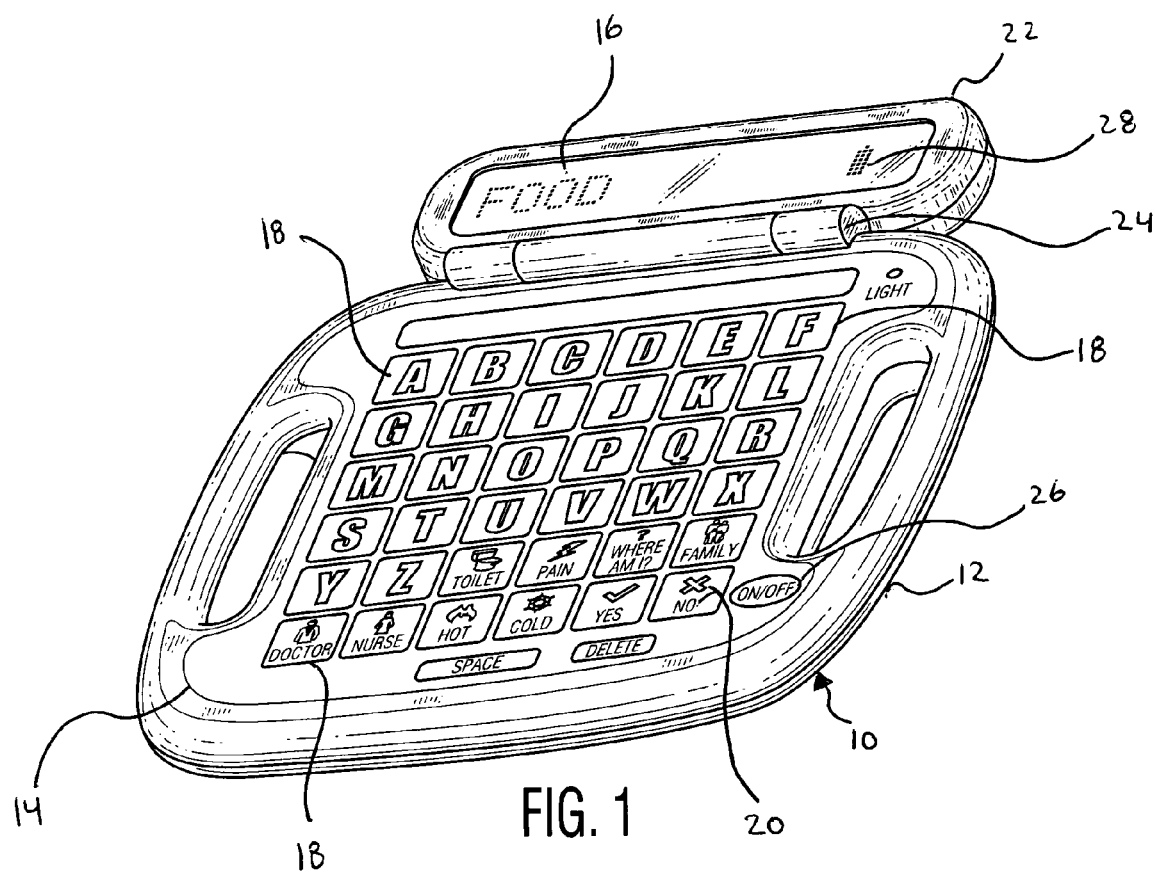
FIG. 1 shows a first side of a representative hand-held communication device.
Figure 2:
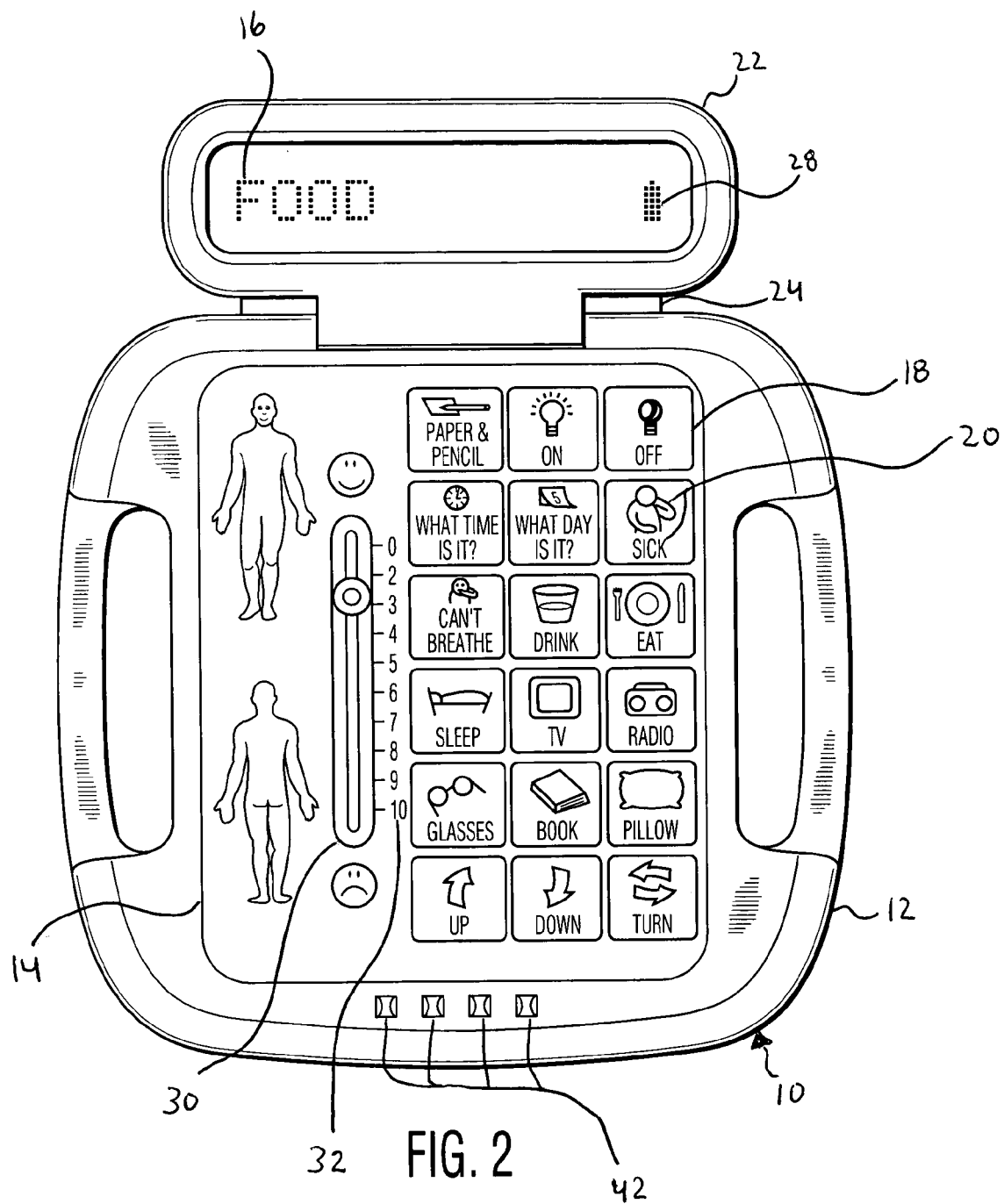
FIG. 2 shows a second side of a representative hand-held communication device.

Referring to FIG. 1, the hand-held communication device 10 comprises a housing 12. The housing 12 comprises a first side and second side. The first side of the housing 12 is the side which faces the voice-disabled person when using the device 10 (see, FIG. 1). The second side of the housing 12 is the side that is opposite the first side of the housing 12, and generally faces away from the voice-disabled user (see, FIG. 2). The housing 12 of the communication device 10 is generally lap-sized and is, thus, portable. The shape of the housing 12 is not limited; however, the shape is generally rectangular. In some embodiments, the dimensions of the housing 12 of the communication device 10 are approximately from 7 to 11 inches long, from 6 to 10 inches wide, and from ½ to 2½ inches deep. The housing 12 can be made from a number of materials including, for example, a durable lightweight polycarbon plastic.

Also referring to FIG. 1, the hand-held communication device 10 also comprises a plurality of means for receiving physical input 14. Each physical input receiving means 14 generates a specified response signal 16 upon being physically manipulated. In some embodiments, the means for receiving physical input 14 comprises a key pad or a touch pad. The key pad can comprise one or more keys 18. In some embodiments, a first key pad can be located on the first side of the housing 12. In some embodiments, a second key pad can be located on the second side of the housing 12. In some embodiments, both the first side and second side of the housing 12 comprises a key pad.

Also referring to FIG. 1, the keys 18 of the key pad(s) can each comprise a descriptive word, phrase, or picture 20, or any combination thereof, printed or embossed onto the surface thereof. For example, a plurality of keys 18 of a key pad may comprise, collectively, the letters of the alphabet, A-Z, and/or numerals 0-9. Alternately, the keys 18 of a key pad may represent particular commands, requests, or information related to the voice-disabled user. For example, individual keys 18 may contain a descriptive word, phrase, and/or picture 20 embossed or printed thereon for numerous commands, requests, or information including, but not limited to: doctor, nurse, hot, cold, up, down, hungry, thirsty, family, turn, bed, chair, toilet, sit, bath, sleep, sick, TV, dizzy, book, pillow, yes, no, on, off, glasses, lotion, hairbrush, light, cannot breath, paper and pencil, and the like, or any combination thereof. In addition, a key may be labeled with a particular question such as, for example, "what day is it?", "what time is it?", "where am I?", or any combination thereof. Further, the key pad(s) of the invention may comprise any combination of the foregoing keys 18. For example, the key comprising the descriptive word "bed" may also have a picture of a bed associated therewith. Likewise for the other keys 18 and descriptive words and pictures 20. Additional keys 18 can be printed or embossed with textual functions such as, for example, a space or delete function. In addition, the keys 18 of the key pad can be printed or embossed in any language(s) desired. The commands and questions displayed can, of course, be replaced by any number of synonyms. For example, "hungry" can easily be replaced with "eat" and "thirsty" can easily be replaced with "drink." All such synonyms are within the spirit of the invention.

Figure 5A:
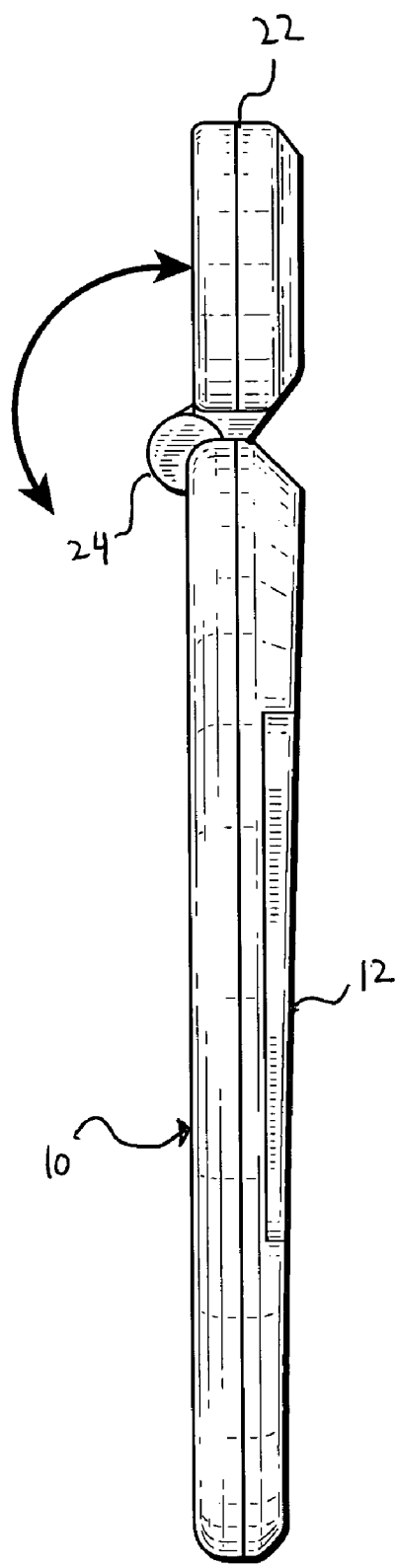
FIG. 5A shows a side view of a representative hand-held communication device wherein the display means is in an extended position.
Figure 5B:
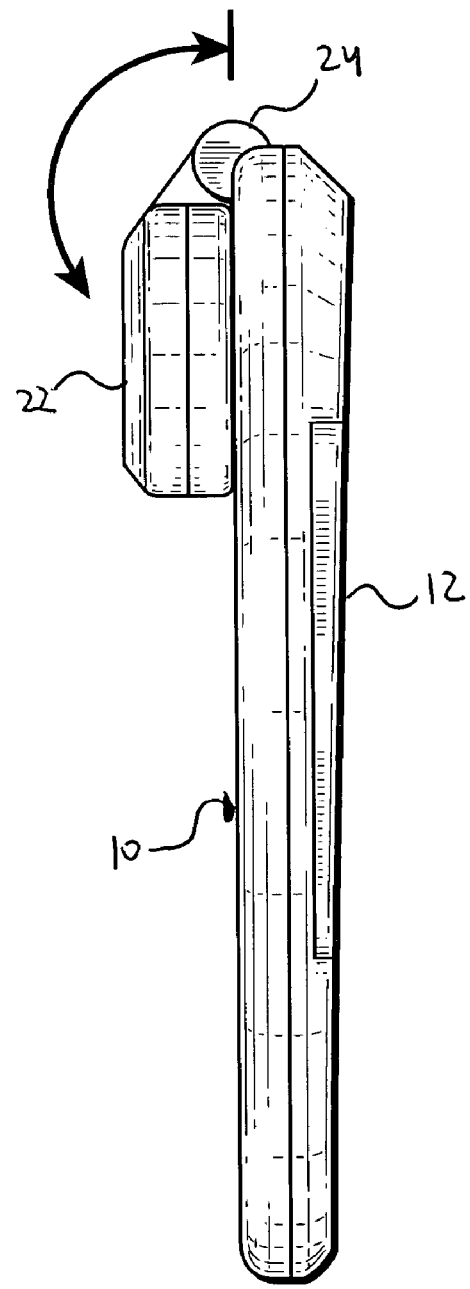
FIG. 5B shows a side view of a representative hand-held communication device wherein the display means is in a closed position.

Also referring to FIG. 1, the hand-held communication device 10 also comprises a display means 22 comprising a first and second side. The display means 22 displays the specified response signal 16 in a textual manner generated by the voice-disabled user physically manipulating the keys 18 of the keypad. In some embodiments, the display means 22 is or comprises a display screen having a first and second side. In some embodiments, the display means 22 is connected to the housing 12 by a hinge means 24. In some embodiments, the display means 22 is pivotally mounted to the housing 12. The display means 22 can, thus, be positioned in an extended position in which the display means 22 is positioned in the same plane as the housing 12 (see, FIG. 5A) or in a folded closed position in which the first (front) side of the display means 22 faces the first side of the housing 12 (see, FIG. 5B). In some embodiments, the display means displays visual representations of the specified response signal 16 on the first and second side thereof. In this manner, the voice-disabled user can visualize the text of his or her command, for example, on the display means 22 and the recipient of the command facing the voice-disabled user can also visualize the text of the command on the other side of the display means 22. The display means 22 can be made of a hardened clear plastic or LCD surface. The display means 22 can be backlit and its contrast can be optionally adjustable with a manual dial (not shown) located anywhere on the device 10, preferably in the lower right hand position. In some embodiments, the display means 22 is approximately from 1 to 2 inches long, from 4 to 6 inches wide, and from ¼ to 2 inches deep.

Also referring to FIG. 1, the hand-held communication device 10 also comprises means for receiving the response signals and converting the response signals into a corresponding visual representation on the display means (not shown). In some embodiments, the means for receiving the response signals and converting the response signals into a corresponding visual representation on the display means comprises electronic circuitry. In some embodiments, the electronic circuitry is computer controlled. The display means 22 is in electronic communication with the keys 18 of the key pad.

The communication device 10 activates when the display means 22 is touched and/or when a manual on/off switch 26 is in the "on" position. The manual on/off switch 26 can be located anywhere within the device 10.

The communication device 10 also comprises a built-in, preferably rechargeable, battery and compartment therefore with an AC adapter (not shown) for both portable and plugged-in operating service. The hand-held communication device 10 may also comprise a battery level indicator 28, which may be located anywhere on the device 10. In one embodiment, the battery level indicator 28 is positioned on the display means 22 as a series of LCD dots arranged in columns and rows. As the battery loses power, the number of LCD dots that remain lit diminishes. In one embodiment, the battery level indicator 28 has three dots across and six dots up and down, the middle dots disappear as the battery life is diminished. Once the battery has ⅛ battery level remaining, the battery level indicator 28 can flash, and then shut the device 10 down at 1/16 power remaining. In some embodiments, to save battery life, the device 10 can go into a energy conserving "sleep" mode if the device 10 sits inactive for a set period of time, such as three minutes. Upon touching the display means 22 or other functionality, the device 10 can reactivate itself showing the last displayed message. In some embodiments, the battery can have a continuous use of about two to eight hours.

In some embodiments, the second side of the housing 12 further comprises a pain indicator 30, which may further comprise a pain scale 32. The pain scale 32 may comprise, for example, a series of LCD dots, the number of which are activated may indicate the level of pain.

Figure 3:
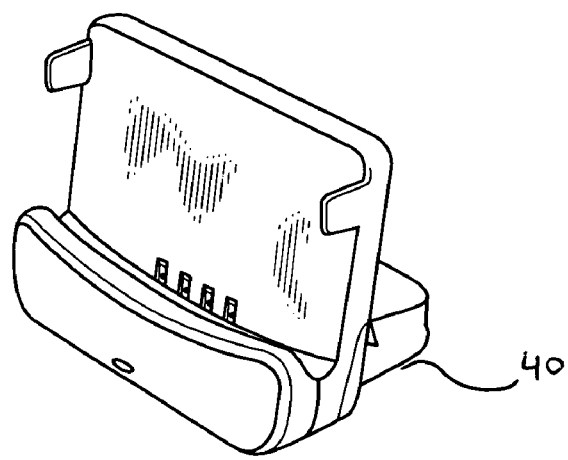
FIG. 3 shows a representative charging station for a typical hand-held communication device.
Figure 4:
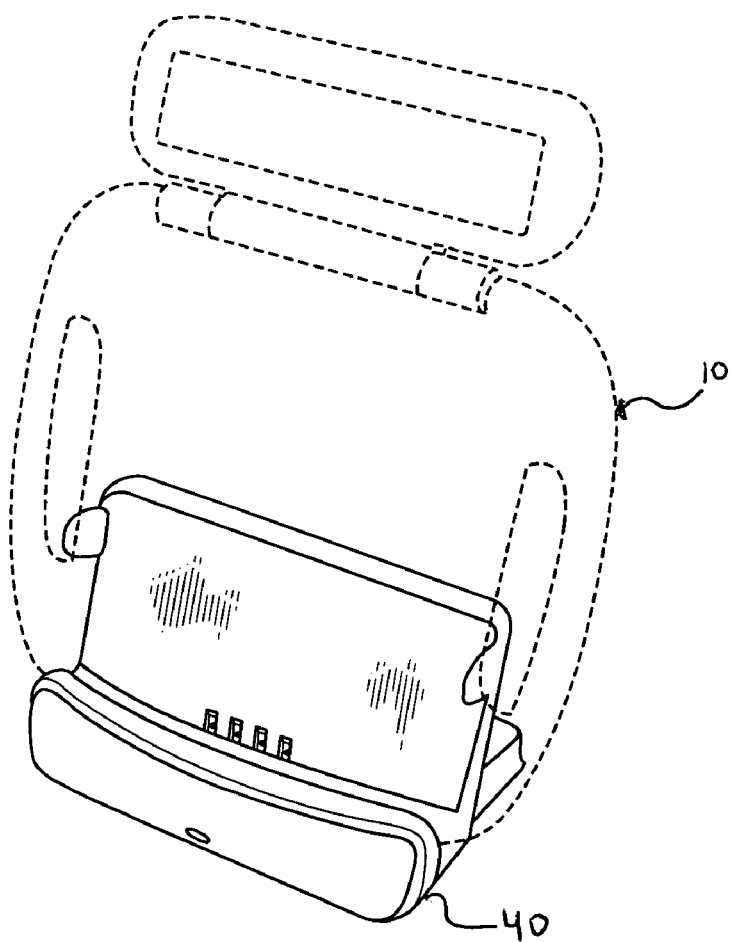
FIG. 4 shows an interaction between the representative charging station and a typical hand-held communication device.

In some embodiments, the hand-held communication device 10 further comprises a recharging station 40 (see, FIG. 3). The recharging station 40 interacts with recharging posts 42 located on the housing 12 of the device 10 (see, FIG. 4). The recharging posts 42 on the housing 12 are in recharging communication with the battery or batteries.

Various modifications of the invention, in addition to those described herein, will be apparent to those skilled in the art from the foregoing description. Such modifications are also intended to fall within the scope of the appended claims.

What is claimed is:

1. A hand-held communication device comprising:
   a housing comprising a first and second side;
   a plurality of means for receiving physical input, wherein the means for receiving physical input comprises a key pad comprising one or more keys, each physical input receiving means generating a specified response signal upon being physically manipulated;

a display means comprising a first and second side; and means for receiving the response signals and converting the response signals into a corresponding visual representation on the display means;

wherein the key pad comprises a key for each letter of the alphabet and/or a key for numerals 0 to 9;

wherein the key pad comprises a descriptive word, phrase, or picture selected from the group consisting of: doctor, nurse, hot, cold, "what day is it?", up, down, hungry, thirsty, family, turn, bed, chair, toilet, sit, bath, "what time is it?", sleep, sick, TV, dizzy, book, pillow, yes, no, on, off, "where am I?", glasses, lotion, hairbrush, light, cannot breath, paper and pencil, or any combination thereof; and wherein the second side of the housing further comprises a pain indicator.

2. The hand-held communication device of claim 1 wherein the display screen is an LCD screen.

3. The hand-held communication device of claim 1 wherein the second side of the housing further comprises a pain indicator.

4. The hand-held communication device of claim 1 in combination with a recharging station.

5. The hand-held communication device of claim 1 wherein the key pad is located on the first side of the housing.

6. The hand-held communication device of claim 5 wherein a second key pad is located on the second side of the housing.

7. The hand-held communication device of claim 1 wherein the display means is a display screen.

8. The hand-held communication device of claim 7 wherein the display screen is pivotally mounted to the housing.

9. The hand-held communication device of claim 7 wherein the display screen displays visual representations on the first and second side.

10. The hand-held communication device of claim 1 wherein the means for receiving the response signals and converting the response signals into a corresponding visual representation on the display means comprises electronic circuitry.

11. The hand-held communication device of claim 10 wherein the electronic circuitry is computer controlled.

12. The hand-held communication device of claim 1 wherein the keys of the key pad comprise a descriptive word, phrase, or picture printed onto at least one surface thereof.

13. The hand-held communication device of claim 12 wherein the key pad comprises a key for each letter of the alphabet, a key for numerals 0 to 9, and a descriptive word, phrase, or picture selected from the group consisting of: doctor, nurse, hot, cold, "what day is it?", up, down, hungry, thirsty, family, turn, bed, chair, toilet, sit, bath, "what time is it?", sleep, sick, TV, dizzy, book, pillow, yes, no, on, off, "where am I?", glasses, lotion, hairbrush, light, cannot breath, paper and pencil, or any combination thereof.

14. The hand-held communication device of claim 1 wherein the housing further comprises a battery compartment.

15. The hand-held communication device of claim 14 wherein the housing further comprises a battery level indicator.

* * * * *

UNITED STATES PATENT AND TRADEMARK OFFICE
CERTIFICATE OF CORRECTION

PATENT NO. : 7,659,836 B2  Page 1 of 1
APPLICATION NO. : 11/186159
DATED : February 9, 2010
INVENTOR(S) : Kathleen Novak It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1238 days.

Signed and Sealed this

Thirtieth Day of November, 2010

David J. Kappos
*Director of the United States Patent and Trademark Office*